United States Patent [19]

Hopf et al.

[11] Patent Number: 4,735,885

[45] Date of Patent: Apr. 5, 1988

[54] DEEP UV PHOTORESIST COMPOSITION WITH 1,3-DISUBSTITUTED-5-DIAZOBARBITURIC ACIDS

[75] Inventors: Frederick R. Hopf, Parsippany; Michael J. McFarland, Middlesex, both of N.J.

[73] Assignee: Allied Corporation, Morris Township, Morris County, N.J.

[21] Appl. No.: 805,641

[22] Filed: Dec. 6, 1985

[51] Int. Cl.$^4$ .............................................. G03C 1/54
[52] U.S. Cl. .................................. 430/192; 430/165; 430/170; 430/193; 430/326
[58] Field of Search ............... 430/193, 156, 312, 326, 430/170, 165, 192

[56] References Cited

U.S. PATENT DOCUMENTS

| | | |
|---|---|---|
| 3,849,137 | 11/1974 | Barzynski et al. |
| 4,207,107 | 6/1980 | Ross ..................... 430/193 |
| 4,339,522 | 7/1982 | Belanson et al. ............... 430/193 |
| 4,414,059 | 11/1983 | Blum et al. |
| 4,427,760 | 1/1984 | Nagazawa et al. .................. 430/287 |
| 4,517,275 | 5/1985 | Stahlhofen ........................ 430/193 |
| 4,522,911 | 6/1985 | Clecak et al. .................. 430/193 |
| 4,588,670 | 5/1986 | Kelly et al. ................... 430/193 |

FOREIGN PATENT DOCUMENTS 0129694 1/1985 European Pat. Off. .
2099168 12/1982 United Kingdom .

OTHER PUBLICATIONS

German Publication Agnew Chem. 92(9), 754–55, (1980).
V. Papesch, et al., Pyrimido[5,4-d] [1,2,3]Triazines, J. Org. Chem., vol. 28, pp. 1329–1331 (1963).
Von Egon Fahr, Dihydrodiazoanhydride, Ann., vol. 627, pp. 213–217 (1959).

Primary Examiner—Charles L. Bowers, Jr.
Attorney, Agent, or Firm—Harold N. Wells; Jay P. Friedenson

[57] ABSTRACT

Disclosed are substituted derivatives of 5-diazobarbituric acid selected from those having the formulas:

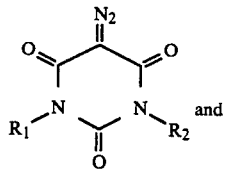

and

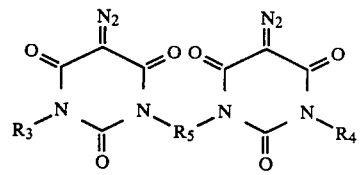

wherein $R_1$ and $R_2$ are substituents selected from the group consisting of $C_3$ to $C_{12}$ alkyl, cyclohexyl, benzyl and $C_2$ to $C_6$ aralkyl groups, wherein $R_3$ and $R_4$ are substituents selected from the group consisting of $C_1$ to $C_{12}$ alkyl, cyclohexyl, benzyl or other $C_2$ to $C_6$ aralkyl groups and $R_5$ is selected from the group consisting of $\alpha,\omega$-disubstituted $C_2$ to $C_{12}$ alkyl, methylene dicyclohexyl, or $C_1$ to $C_6$ dialkylphenylene.

These compounds provide DUV response with an absorption maximum near 260 nm. The substituents are chosen to be nonabsorbing alkyl groups that allow efficient photobleaching of the sensitizer during exposure.

The sensitizers of the present invention are designed to function in the DUV region and are useful in the manufacture of semi-conductor devices.

14 Claims, 1 Drawing Sheet

DEEP UV PHOTORESIST COMPOSITION WITH 1,3-DISUBSTITUTED-5-DIAZOBARBITURIC ACIDS

BACKGROUND OF THE INVENTION

1. Field of the Invention

This invention relates to novel barbituic acid compounds and more particularly to such compounds which are useful as deep ultraviolet (DUV) photorest sensitizers, to a general method of synthesis for these sensitizers, to positive photoresist compositions incorporating said sensitizers and to the method for providing positive photoresist layers which incorporate these sensitizers.

The invention contemplates the provision of novel barbituic compounds, per se, although the invention will be described primarily with reference to the use of compounds of this kind with reference to positive photoresist compositions and to the application thereof in the manufacture of semiconductor components.

2. Description of the Prior Art

Photoresists are materials which change their solubility in a developer solution after the photoresist has been exposed to actinic radiation, such as to ultraviolet radiation. Photoresist compositions comprise a photosensitive compound (hereafter sometimes called sensitizer or photosensitizer), a film forming polymeric resin and a solvent. There are other types of compositions possible, such as a photosensitive polymer in an appropriate solvent for example. The photoresist composition is applied to a substrate which is to be patterned and the solvent is then usually removed, as with heat, leaving the photoresist as a thin film covering the substrate. As a consequence of the exposure to radiation of the photoresist, a different solubility rate results between the exposed and unexposed (masked over) portions of a resist film that yields a surface relief pattern after the development. Thoses photoresists which become more soluble in a developer solution in the exposed regions are referred to as "positive" photoresists. Those which become less soluble in the exposed regions are referred to as "negative" photoresists. The present invention deals with a class of those compounds suitable for use in positive photoresist compositions.

Positive photoresists typically comprise an aqueous alkali soluble resin, such as novolac resin or poly(p-hydroxystyrene), and a diazonaphthoquinone sulfonic acid ester sensitizer. The resin and sensitizer are applied such as by spin coating, spray coating, or other suitable means from an organic solvent or solvent mixture onto a substrate, such as a silicon wafer or a chromeplated glass plate. The developer used to process the positive photoresists are aqueous alkaline solutions, such as sodium metasilicate, potassium hydroxide, tetramethyl ammonium hydroxide and ammonium hydroxide. The developer removes the areas of the coated photoresist film that have been exposed to light or other form of irradiation so as to produce a relief pattern in the photoresist film.

The application of a photosensitive film to various substrates is an essential step in the fabrication of integrated circuits. The substrates are generally silicon wafers which may have a thin oxide coating or other coating such as silicon nitride or aluminum. The photosensitive film is used to pattern the substrate in a series of steps including exposure (through a mask pattern), development to yield a relief pattern in the resist layer and substrate etch to transfer that pattern into the substrate material. It is essential that the mask pattern be accurately reproduced in the substrate etch pattern. To achieve this high degree of accuracy, the mask pattern must be well resolved by the photoresist layer. The laws of optics and diffraction dictate that resolution will improve as the wavelength of the irradiation is shortened. Thus, photoresists capable of operating in the deep ultraviolet (DUV) region (200–300nm) will be capable of higher potential resolution than those resists limited to operating in the near ultraviolet (NUV) region (300–400nm). Conventional photoresists employing novolac resins as the alkali soluble, film forming polymers are highly absorbing in the DUV region in films of approximately one micron thickness and so cannot be used in that region. Diazonaphthoquinone sulfonic acid esters are commonly used as sensitizers in conventional NUV photoresists. While these ester sensitizers are photoactive in the DUV, they exhibit several serious limitations for use as DUV photosensitizers. These sensitizers exhibit intense absorptions in the DUV region, making the resist composition excessively absorptive as well. These DUV absorptions are also poorly photobleached by the exposing radiation so that the film's absorbance is not greatly diminished during the irradiation process. Ideally, the sensitizer photoproduct should be nonabsorbing in the region of irradiation used to expose the resist so that all absorbed light does useful chemistry, thereby maximizing sensitivity. These prior art sensitizers also possess NUV absorption bands which allow them to be used in conventional NUV photoresists. However, this NUV response would be considered a drawback in a true DUV resist, as it would necessitate filtering the exposure source to remove long wavelength radiation to prevent degradation of the resolution.

Accordingly, it is apparent that a need exists for new photosensitive compounds and for formulations which contain sensitizers designed specifically to operate effectively in the DUV spectral region during the process of integrated circuit manufacture. The present invention discloses a class of compounds which is especially well suited to perform in the desired region.

Other attempts have been made to design a photoresist system for the DUV region. For example, Reichmanis, Wilkins, Chandross and Gooden, as described in UK Patent Application No. 2,099,168 have demonstrated several systems based on the photochemistry of ortho-nitrobenzyl groups attached to both polymers and sensitizer molecules. Another disclosure is that of the use of orthonitrobenzyl chemistry for photoresists as in U.S. Pat. No. 3,849,137.

Chemistry suitable for DUV photoresists also includes that of chain scission of high molecular weight polymer into lower molecular weight polymer. In this case, the energy of the DUV light is sufficient to rupture bonds in the polymer chain, resulting in lower molecular weight material of increased solubility. The most common example of this technique uses poly(methyl methacrylate). The primary drawbacks of this resist are the need for high exposure doses to yield a sufficient difference in molecular weights and the need to use an organic solvent as the developing medium.

Another example of DUV photoresist technology involves the use of DUV excimer lasers of high instantaneous fluence to ablate away selected areas of the photoresist film. This technique has been referred to as laser photo-ablation. See, for example, the U.S. Pat. No. 4,414,059.

Still another disclosure relating to DUV sensitizers is found in European Patent Application No. 0 129 694, which describes compounds based on diazohomotetramic acid for use in photoresist compositions.

Further background on photoresist processes and requirements, including reference to photoresists especially designed for the DUV region is presented in the American Chemical Society Symposium Series #266, *Materials for Microlithography*, L. F. Thompson, Ed., ACS 1984, M. J. Bowden, "A Perspective on Resist Materials for Fine-Line Lithography".

Also, while the 1,3 dimethyl-5-diazobarbituric acid has been disclosed by Von Bruno Kokel, et al. in the German publication *Angew. Chem.* 92(9) 754 (1980), neither the compounds of the invention nor the usefulness as sensitizers for the positive photoresist composition has been known prior to our discovery.

SUMMARY OF THE INVENTION

In accordance with the invention, a novel class of compounds and their use as positive photoresist sensitizers is provided which exhibits superior light sensitivity performance in the deep ultraviolet region The novel sensitizers of the present invention comprise the substituted derivatives of 5-diazobarbituric acid selected from the monochromophoric and bichromophoric derivatives, respectively, having the structural formulas:

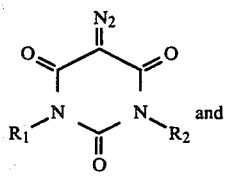

and

wherein $R_1$ and $R_2$ are substituents selected from the group consisting of $C_3$ to $C_{12}$ alkyl, cyclohexyl, benzyl, and $C_2$ to $C_6$ aralykyl groups, $R_3$ and $R_4$ are substituents selected from the group consisting of $C_1$ to $C_{12}$ alkyl, cyclohexyl, benzyl and $C_2$ to $C_6$ aralkyl groups and $R_5$ is selected from the group consisting of $\alpha,\omega$-disubstituted $C_2$ to $C_{12}$ alkyl, methylene dicyclohexyl or $C_1$ to $C_6$ dialkylphenylene groups.

Specific compounds of the invention when employed in positive photoresist formulations provide only DUV response with an absorption maximum at about 260 nm. In addition, these specific compounds contain non-absorbing alkyl groups that allow efficient photobleaching of the sensitizer during exposure.

Because the sensitizers of the present invention are designed to function only in the DUV region, they require the use of appropriate photoresist resins for workable admixtures. The novolac type resins that are used in the NUV resists, for example, are not suitable due to their high absorbance (opacity) in this spectral region. Useful resins which may be used are the aqueous alkaline soluble resins which include copolymers of maleimide with 4-isopropylstyrene or 4-ethylstyrene or 4-methylstyrene or 2,4-dimethylstyrene or styrene or a resin consisting of a homopolymer of maleimide. Resins of this kind are described, for example, in co-pending commonly assigned U.S. application of F. R. Hopf. et. al., Ser. No. 547,815, filed Nov. 1, 1983. These resins possess the attributes necessary for a DUV photoresist resin. Such attributes include low absorbance in the spectral region of interest, solubility in aqueous alkaline developer solution, compatability with the photoresist sensitizer and solvent, ability to form a film by spin coating from an appropriate photoresist solvent, adhesion to the substrate, thermal stability to the processing conditions, physical and chemical stability to the substrate etching conditions and ease of removal from the substrate at the conclusion of processing. These resins are known to form useful photoresist compositions with the photosensitizers of the present invention. A typical resin used in Examples 1-10 of the present invention, consists of a 1:1 copolymer of 4-tert-butylstyrene and maleimide. The use of the sensitizers of the invention is not limited to use with any particular resin or those described as illustrative; the sensitizers of the invention are capable of being used with other polymeric resins which fulfill the requirements of a DUV photoresist resin as described hereinabove.

The sensitizer compounds of the invention used in preparing the photoresist formulations are blended in a polymer/sensitizer ratio ranging from about 3:1 to 10:1 (by weight) with a suitable polymer and solvent useful for forming films of the mixture, e.g. 4-tert-butylstyrene/maleimide copolymer in 2-methoxyethyl ether (diglyme). The mixture may be applied by spin coating onto silicon wafers and then baked to remove the diglyme leaving dry films of approximately 1 $\mu$m thickness. The film is exposed through a resolution mask, e.g. chrome on quartz, to approximately 50 mJ/cm² of DUV irradiation centered at 260 nm. The exposed films are then developed in aqueous alkaline medium to produce a positive relief image, i.e. with good film retention in the unirradiated areas and complete clearing to the substrate in the irradiated areas.

DESCRIPTION OF THE PREFERRED EMBODIMENT

Figure 2:
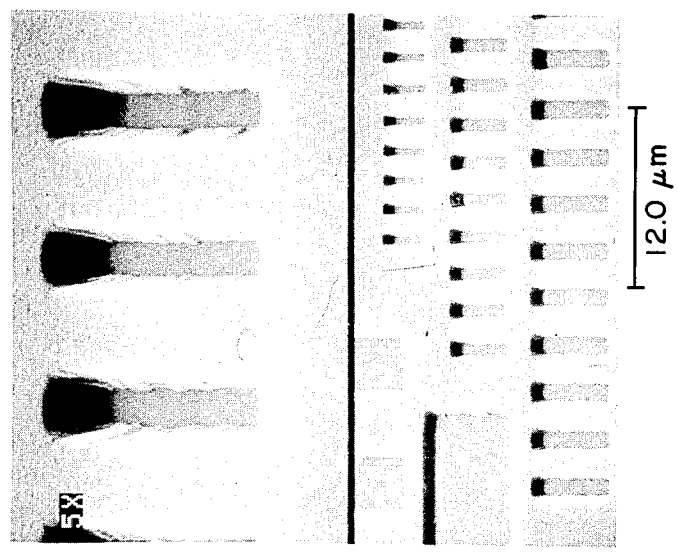
FIG. 2 is a scanning electron microscope showing developed image holes in the resist film on a silicon substrate.

In producing the novel photoresist composition of the invention the key ingredient of the photoresist is the novel diazobarbituric acid photo sensitizer compound that is incorporated into the sensitizer-resin-solvent composition. In accordance with the present invention the sensitizer compounds, which upon exposure to light (in the appropriate spectral region) become more soluble in aqueous alkaline developers, comprise the 1,3-disubstituted-5-diazobarbituric acids, i.e., monochromophoric structures of the formula:

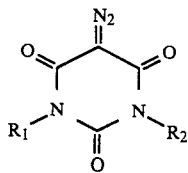

and bichromophoric structures of the formula:

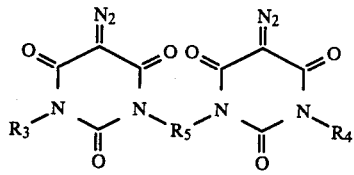

wherein $R_1$ and $R_2$ are substituents selected from the group consisting of $C_3$ to $C_{12}$ alkyl, cyclohexyl, benzyl and $C_2$ to $C_6$ aralkyl groups, wherein $R_3$ and $R_4$ are substituents selected from the group consisting of $C_1$ to $C_{12}$ alkyl, cyclohexyl, benzyl and $C_2$ to $C_6$ aralkyl groups and $R_5$ is selected from the group consisting of $\alpha,\omega$-disubstituted $C_2$ to $C_{12}$ alkyl, methylene dicyclohexyl or $C_1$ to $C_6$ dialkylphenylene.

The substituents of these compounds can be selected so that a compound may exhibit only DUV absorption with maxima at about 260 nm. The substitutions may be selected so as to impart NUV absorption as well. In the preferred embodiments, alkyl substituents have been employed to achieve the desired properties, as with $R_1=R_2=$cyclohexyl; $R_3=R_4=$butyl and $R_5=$dodecyl; or $R_3=R_4=$cyclohexyl and $R_5=$dodecyl. Included among the particular preferred diazobarbituric acid compounds are: 1,3-dicyclohexyl-5-diazobarbituric acid; 1,12-bis(3-[1-cyclohexyl-5-diazo-2,4,6(1H,3H,5H)-pyrimidenetrionyl])dodecane; 1,12-bis(3-[1-n-butyl-5-diazo2,4,6(1H,3H,5H)-pyrimidinetrionyl]) dodecane; 1-(1-butyl)-3-cyclohexyl-5-diazobarbituric acid; and the bichromophoric compound of the above formula wherein $R_3$ and $R_4$ are cyclohexyl and $R_5$ is methylene dicyclohexyl.

Typically these diazobarbituric acid sensitizers are compounded in a suitable polymer/sensitizer ratio with an alkali soluble polymer in a spinning solvent and spun onto Si wafers to produce films with a dry thickness of approximately 1 $\mu$m. In the preferred embodiment, any of the five sensitizers listed immediately above is compounded with 4-tert butyl styrene/maleimide copolymer such that the resin to sensitizer ratio is 7:1 by weight. The preferred solvent is 2-methoxyethyl ether (diglyme) and the percent solids in the diglyme is 25 to 35% by weight depending on the film thickness that is desired. After spin coating the substrate with resist, the wafers are baked to remove the solvent; 30-40 minutes at 80° C. in a convection oven is preferred. After the bake, the film is exposed to DUV light through a chrome on quartz photomask. The preferred irradiation is 40-60 mJ/cm$^2$ of DUV light centered at 260 nm to match the absorbance of the sensitizer. After exposure, the photoresist is developed in aqueous alkaline solution to remove those areas of the film exposed to the DUV light and thereby produce a positive relief image in the photoresist layer.

The sensitizer acts to decrease the solubility of the photoresist resin in the alkaline developer. Upon exposure to light, the sensitizer undergoes a photochemical reaction to produce a new form which will not protect the resin from dissolution in the alkaline developer. The form of the photoreacted sensitizer is presumed to be an alpha-keto carboxylic acid, at least in the initial stages after exposure.

The resin utilized in the resist is the film forming component and physical vehicle for the sensitizer. As listed above, the resin must possess a number of characteristics in order to perform well as a DUV photoresist polymer. The maleimide copolymers with substituted styrenes are given as examples of suitable resins for this application.

The solvent used in preparing the novel photoresist composition of the invention is characterized by having good solubility for the resin and the sensitizers. Preferably also, the solvent composition should result in minimal striations and excellent wetting properties. In addition to diglyme, other suitable solvents include dimethyl formamide, N-methyl pyrrolidone, and cyclohexanone. The solvent composition may also comprise a mixture of suitable solvents.

The invention will be further described by the following examples. It is to be understood, however, that although these examples may describe in detail certain preferred embodiments of the invention, they are given primarily for purposes of illustration and the invention in its broader aspects is not limited hereto.

GENERAL PROCEDURE

Resists were compounded in dyglyme so that the solids constituted 32% of the solution by weight. Resist solutions were filtered through 0.2 $\mu$m PTFE filters (Schleicher and Schuell) into clean glass containers. Substrates were polished silicon wafers (Pensilco) or polished silicon wafers with a layer of thermally grown silicon dioxide (Semimetals). The substrates were cleaned before use and exposed to ten minutes vapor treatment with 1,1,1,3,3,3-hexamethyldisilazane (HMDS), a common wafer pretreatment. The substrates were mounted on the vacuum chuck of a Headway Research spinner (model EC-101) and photoresist solution was applied to the wafers with a pipette. Films were spun so as to give a thickness of approximately 1 $\mu$m after baking. Typically, this involved a spin speed of 6000 rpm for 40 seconds. After spinning, the resist coated wafers were baked for 40 minutes at 80° C. in a convection oven. After baking, the wafers were exposed to DUV light through a resolution mask in the contact mode. Irradiation was carried out with an OAI (Optical Associates) Series 30 lightsource fitted with 260 nm optics. Lamp output was further filtered with a 260 nm broad band filter (Omega Optical, 50 nm FWHM) to insure that only DUV irradiation fell on the resist. The mask was chrome on quartz (Ditric Optics) with feature sizes ranging down to a nominal 1 $\mu$m. Irradiation intensity, after the secondary filter, was calibrated with an Eppley thermopile. The loss of film in the unirradiated areas was determined by measuring the thickness of those areas before and after development with a Rudolf FTM interferometric film thickness monitor. Developed images were examined by both optical and electron microscopy.

EXAMPLE 1

1,3-dicyclohexyl-5-diazobarbituric acid was compounded in a polymer/sensitizer ratio of 6:1 (w:w) with 4-tert-butylstyrene/maleimide copolymer in diglyme as a spinning solvent. The polymer was produced by a free radical polymerization. Resist was spun on Si wafers to produce films with a dry thickness of approximately 1 μm after baking 40 minutes at 80° C. The dry films were exposed through a positive mask with 60 mJ/cm$^2$ of DUV light centered at 260 nm. The exposed films were developed for 60 seconds in 0.20 N aqueous potassium hydroxide (KOH) at room temperature to produce a positive relief image with 81% film retention in the unirradiated areas.

EXAMPLE 2

A resist was prepared in the manner of Example 1 except that the resin/sensitizer ratio was changed to 7:1 (w:w). The resist film was prepared in the same manner as in example 1. The film was exposed to 48 mJ/cm$^2$ of DUV light at 260 nm through a positive mask. The exposed film was developed for 230 seconds in 0.14 N KOH solution. A positive relief image was produced with 75% film retention.

EXAMPLE 3

(Comparative)

A resist was prepared according to the procedure of Example 1, except that the sensitizer was 1,3-dimethyl5-diazobarbituric acid. The resist film was prepared in the same manner as Example 1. The film was exposed to 80 mJ/cm$^2$ of DUV light at 260 nm through a positive mask. The exposed film was developed for 90 seconds in 0.15 N tetramethyl ammonium hydroxide to produce a relief image with only 21% film retention. (This is roughly 4 times less retention than that of Example 1, even though the exposure was greater.) Thus, although the compound wherein $R_1=R_2$=methyl has been previously prepared, but not described in any lithographic context, we have shown it to be insufficient to serve in that context anyway. It is necessary for the R groups to be of sufficient size to impart a reasonable hydrophobicity to the resist film for protective purposes.

EXAMPLE 4

A resist was compounded in the manner of Example 2 except the sensitizer was 1,12-bis(3-[1-cyclohexyl-5-diazo-2,4,6 (1H,3H,5H)-pyrimidinetrionyl])dodecane. This comprises a structure as disclosed in the specification wherein $R_3=R_4$=cyclohexyl and $R_5$=1,12-disubstituted dodecane. The resist film was exposed to 48 mJ/cm$^2$ of DUV light through a positive mask. The exposed film was developed for 225 seconds in 0.14 N KOH solution. A positive relief image was produced with 82% film retention. A scanning electron microscope (SEM) photo of this relief image appears as FIG. 1.

Figure 1:
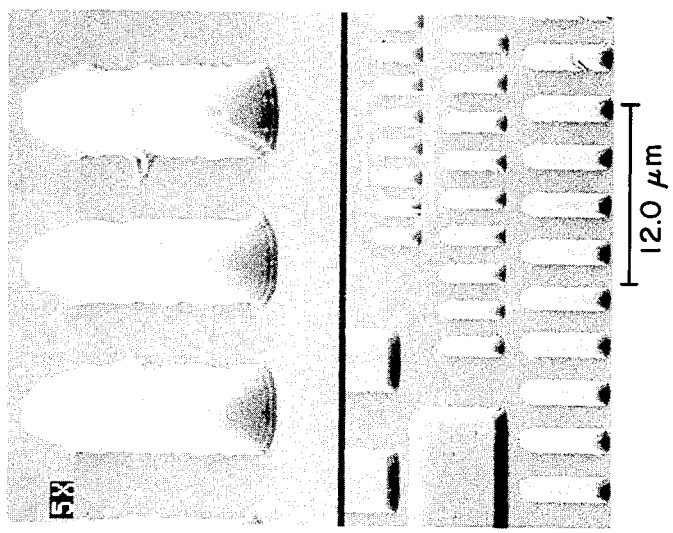
FIG. 1 is a scanning electron microscope photo of the relief image (photoresist lines) of a film prepared with a photoresist composition containing the novel diazobarbituric acid compounds according to the invention. photo

As shown by the SEM (scanning electron microscope) micrographs of imaged relief patterns, FIG. 1 shows free-standing photoresist lines on silicon substrate while FIG. 2 shows developed image holes in resist film on silicon. It is noted that the features are well cleared out with no residue. Each Figure (photo) comprises a split-screen image; the bottom half is a 2500× enlargement and the top half is a further 5× enlargement (12,500×) of the area indicated in the white box. The marker bar indicates 12 μm on the bottom half and 2.4 μm on the top half of the photos. The smallest features have a nominal width of one micrometer.

EXAMPLE 5

A resist was compounded in the manner of Example 2 except the sensitizer was 1,12-bis(3-[1-n-butyl-5-diazo2,4,6(1H,3H,5H)-pyrimidinetrionyl])dodecane, i.e. the compound wherein $R_3=R_4$=n-butyl and $R_5$=1,12-disubstituted dodecane. The resist film was exposed to 48 mJ/cm$^2$ of DUV light through a positive mask. The exposed film was developed for 135 seconds in 0.14 N KOH solution to produce a positive relief image with 74% film retention in the unirradiated areas.

EXAMPLE 6

A resist was prepared in the manner of Example 2. The film was prepared and exposed in the same manner. The exposed film was then developed 55 seconds in 0.20 N KOH solution to produce a positive relief image with 76% film retention in the unirradiated areas.

EXAMPLE 7

A resist was prepared in the manner of Example 4. The film was prepared and exposed in the same manner. The exposed film was then developed 55 seconds in 0.20 N KOH solution to produce a positive relief image with 77% film retention in the unirradiated areas.

EXAMPLE 8

A resist was prepared in the manner of Example 5. The film was prepared and exposed in the same manner. The exposed film was then developed 30 seconds in 0.20 N KOH solution to produce a positive relief image with 72% film retention in the unirradiated areas.

EXAMPLE 9

A resist was prepared in the manner of Example 4. The film was spun onto a substrate of Si with a layer of silicon dioxide (thermally grown). The oxide layer was 885 nm thick and the wafer was given the same pretreatment with HMDS. The baking and exposure followed the method of Example 4. The exposed film was developed 90 seconds in 0.20 N KOH solution to produce a positive relief image with 72% film retention in the unirradiated areas.

EXAMPLE 10

(Comparative)

In order to establish the lack of response of these sensitizers to conventional NUV light, a resist was prepared as in Example 4. The film preparation was the same, but the irradiation was 200 mJ/cm$^2$ of NUV light centered at 360 nm. The exposed film was developed 120 seconds in 0.20 N KOH solution (approximately twice as long as in Example 6). There was no positive relief image produced as the irradiated and unirradiated areas were of the same thickness. This establishes that the sensitizers of this invention are not responsive in the NUV region, unlike the diazonaphthoquinone sulfonic acid esters used in conventional resists. Thus they would not require the exposure source to be filtered to prevent degradation of the resolution due to the presence of longer wavelength light.

SYNTHESIS OF 1,3-DIALKYL-5-DIAZOBARBITURIC ACIDS

General Procedure

The 1,3-dialkyl-5-diazobarbituric acids may be prepared from appropriate corresponding commercially available isocyanates and primary amines as the starting materials as indicated by the following schematic reactions:

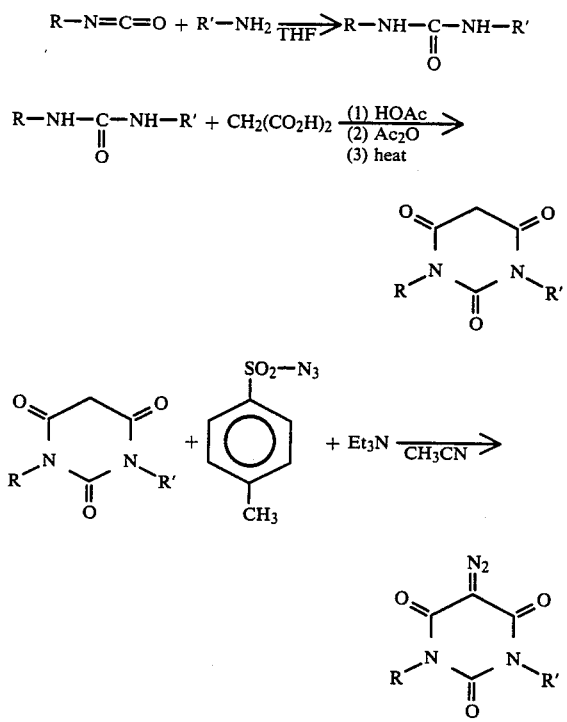

wherein R and R' have the values above ascribed to $R_1$ and $R_2$ respectively.

The synthetic sequence will be illustrated by the steps involved in the synthesis of 1-(1-butyl)-3-cyclohexyl-5-diazobarbituric acid.

EXAMPLE 11

Synthesis of 1-(1-butyl)-3-cylclohexylurea

One hundred mL of tetrahydroguran (THF) was added to a dry 500 mL round bottom 3-neck flask equipped with a thermometer, pressure equalizing addition funnel capped with a drying tube, nitrogen inlet and magnetic stirrer. Then 17.24 mL (0.15 moles) of 98% n-butyl isocyanate was added under nitrogen. A solution of 17.33 mL (0.15 moles) of 99% cyclohexylamine in 46 mL of THF was added to the addition funnel and slowly dropped into the stirred solution of n-butyl isocyanate at a rate (about 20 min.) which maintained the temperature below 40° C. The reaction mixture was stirred for one hour after completion of the addition. The solvent was removed by rotary evaporation. The white residue was vacuum dried for 12 hours at room temperature. The yield of dried, crystalline white product was quantitative. The product melted sharply at 107°–108° C. (uncorrected).

EXAMPLE 12

Synthesis of 1-(1-butyl)-3-cyclohexylbarbituric acid

A solution was prepared by adding 15.87 gm (0.080 mole) of 1-(1-butyl)-3-cyclohexylurea and 8.33 gm (0.080 mole) of malonic acid to 35 mL of reagent grade acetic acid in a 250 mL 3-neck, round bottom flask equipped with a thermometer, pressure equalizing dropping funnel capped by a drying tube, nitrogen inlet and magnetic stirrer. The stirred mixture was gradually heated to 60° C. in a silicone oil bath. All of the solid dissolved before the temperature reached 60° C. A total of 32 mL of acetic anhydride was added to the dropping funnel and slowly (over a period of about 45 min.) dropped into the stirred reaction flask. The temperature was gradually increased to approximately 90° C. for 7 hours, then allowed to cool to room temperature and stand overnight.

The solvent was removed in a heated, water-aspirated rotary evaporator. The crude product was vacuum dried at 50° C. for 24 hours. The slightly yellow crude product (20.7 gm) was isolated in 97% yield. It melted broadly from 103°–106° C. A sample of crude material was recrystallized from hot ethanol/water and dried. These white crystals sublime above 95° C., and melt at 107°–108° C. The crude product was shown to be pure by PMR and IR, and was used for a subsequent synthetic step.

EXAMPLE 13

Synthesis of 1-(1-butyl)-3-cyclohexyl-5-diazobarbituric acid 80 mL of reagent grade acetonitrile and 6.65 gm (0.025 mole) of 1-(1-butyl)-3-cyclohexylbarbituric acid were added to a dry 250 mL 3-neck round bottom flask equipped with a thermometer, pressure equalizing dropping funnel capped by a drying tube, nitrogen inlet and magnetic stirrer. The stirred solution was cooled to 2° C. in an ice bath. Then a solution of 5.75 gm (0.029 mole) of p-toluenesulfonyl azide in 20 mL of acetonitrile was added to the reaction flask. A solution of 3.20 gm (0.0317 mole) of triethylamine in 20 mL of reagent grade dichloromethane was placed in the dropping funnel and slowly added to the reaction flask, while keeping the temperature below 3° C. The flask temperature was kept below 3° C. for 1 hour. The stirred reaction flask was allowed to warm to room temperature (20° C.) and kept at room temperature for 12 hours.

The solvent was rotary evaporated at room temperature. The dark red residue was dissolved in 350 mL of dichloromethane and washed with 350 mL of 5% (w/v) aqueous sodium hydroxide. The dichloromethane solution was washed twice with 300 mL portions of distilled water, dried over anhydrous sodium sulfate and rotary evaporated to dryness. The viscous residue was vacuum dried at 40° C. for 15 hours, the residue remaining was a dark viscous liquid.

The crude material was chromatographed on a silica gel (Brinkman #7733) column packed with dichloromethane. The crude product was added as a dichloromethane solution, initially eluted with dichloromethane to remove unreacted p-toluenesulfonyl azide, then eluted with 2:1 (v/v) dichloromethane/acetonitrile to remove the desired component from the column. After evaporation of solvent, the slightly yellow residue remained a very viscous liquid at room temperature.

SYNTHESIS OF α,ω-BIS (3-[1-ALKYL-5-DIAZO-2,4,6 (1H,3H,5H)-PYRIMIDINETRIONYL]) ALKANES

General Procedure

The above-named compounds were prepared from commercially available starting compounds as indicated by the following schematic reactions:

-continued

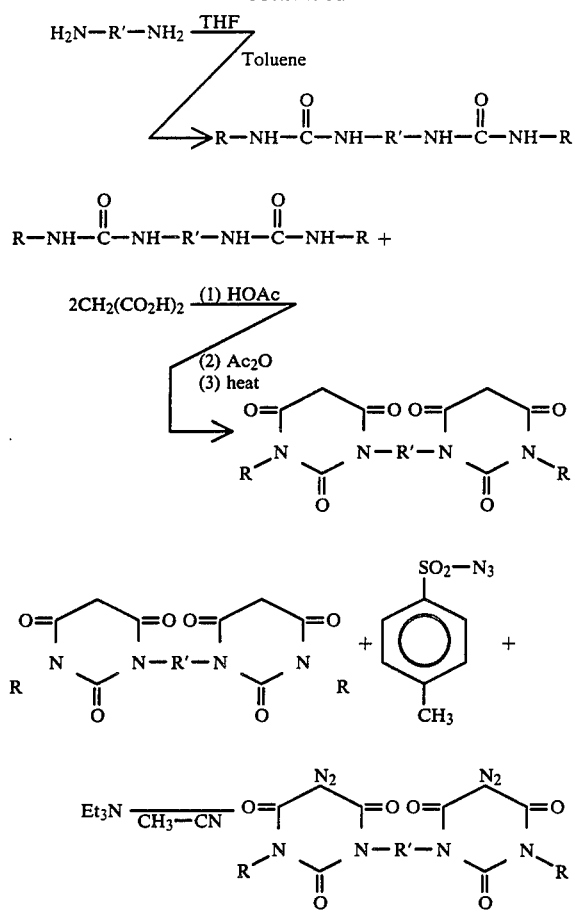

wherein R has the values above ascribed to $R_3$ and $R_4$ and R' has the values above ascribed to $R_5$.

EXAMPLE 14

Synthesis of 1,18-dicyclohexyl-1,3,16,18-tetraaza-2,17-octadecanedione 30.04 gm (0.240 mole) of cyclohexyl isocyanate was dissolved in 400 mL of 1:1 THF/toluene in a 1000 mL round bottom, 3-neck flask equipped with a thermometer, magnetic stirrer, pressure equalizing dropping funnel, nitrogen purge and heating mantle. The solution in the flask was heated to 40° C. 24.04 gm (0.240 mole) of 1,12-dodecanediamine was dissolved in 400 mL of 1:1 THF/toluene and slowly dropped into the stirred, heated solution of isocyanate. After addition of the diamine, an additional 100 mL of toluene was added to the flask. The temperature was raised to 80° C. and the reaction mixture was refluxed for 12 hours.

The solvent was removed with a heated vacuum rotary evaporator. The solid, white product was obtained in quantitative yield. The product was vacuum dried at 50° C. for 15 hours. The quite insoluble product melted sharply at 207°–208° C.

EXAMPLE 15

Synthesis of 1,12-bis(3-[1-cyclohexyl-2,4,6(1H,3H,5H)pyrimidinetrionyl]))dodecane

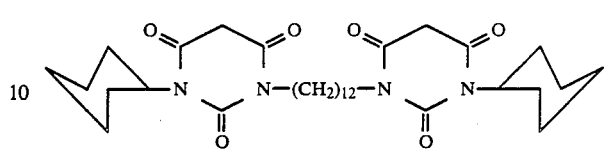

A dry 3-neck, 1000 mL round bottom flask equipped with magnetic stirrer, nitrogen inlet, thermometer and pressure equalizing dropping funnel topped with a drying tube was charged with 900 mL of reagent grade glacial acetic acid. 8.33 gm (0.080 mole) of malonic acid and 18.03 gm (0.040 mole) of 1,18-dicyclohexyl-1,3,16,18-tetraaza-2,17-octadecanedione were added to the flask and it was slowly heated, with stirring, in an oil bath. All of the solids dissolved above a temperature of 85° C. A total of 85 mL of acetic anhydride was slowly dropped into the reaction flask over a period of 1 hour, while the temperature was maintained at 85°–90° C. After acetic anhydride addition, the stirred solution was heated at 90° C. for seven hours, then allowed to cool at room temperature.

The solution was filtered and rotary evaporated to dryness. The solid was vacuum dried at 50° C. for 12 hours. The crude product was isolated in >97% yield. Recrystallization of a sample of crude product caused no significant change in melting point (175°–176° C.), proton magnetic resonance spectrum, infrared spectrum or ultraviolet spectrum.

EXAMPLE 16

Synthesis of 1,12-bis(3-[1-cyclohexyl-5-diazo2,4,6(1H,3H,5H)-pyrimidinetrionyl])dodecane

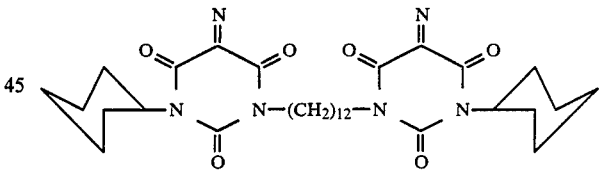

A 3-neck, 1000 mL round bottom flask equipped with magnetic stirrer, thermometer, pressure equalizing dropping funnel and nitrogen inlet was set up for ice bath cooling. 8.88 gm (0.015 mole) of barbituric acid from the preceeding synthetic procedure was dissolved in 75 mL of dichloromethane and placed in the flask. 150 mL of acetonitrile was then added to the solution of barbituric acid. The stirred solution was cooled to 3° C. Then 6.51 gm (0.033 mole) of p-toluenesulfonyl azide in 30 mL of acetonitrile was added to the reaction flask. A solution of 3.58 gm (0.035 mole) of triethylamine in 30 mL of dichloromethane was placed in the dropping funnel and slowly added to the reaction flask over a period of 60 minutes, with the temperature kept below 3° C. Initially, the solution remained clear, but became voilet colored after two hours at 3° C.

After 3 hours at 3° C., the solution was rotary evaporated to dryness with a heating bath temperature of <40° C. The solid reddish residue was vacuum dried at 40° C. for 24 hours. The crude material was dissolved in a minimum of dichloromethane and chromatographed on a column of silica gel (Brinkman #7733) packed with dichloromethane and eluted with dichloromethane/acetonitrile. The middle fraction was retained. A total of 6.8 gm (0.011 mole) of dried product was obtained by evaporation of solvent from the middle cut for a yield of 71%.

While the invention has been described with respect to particular embodiments thereof, it will be understood by those of skill in the art that variations may be made therein without departing from the spirit and scope of the invention.

What is claimed is:

1. A positive photosensitive film forming composition comprising:

(a) from about 2 to about 35 dry weight percent of a substituted derivative of 5-diazobarbituric acid selected from those exhibiting only DUV absorption and having the structural formulas:

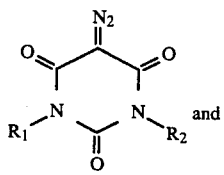

and

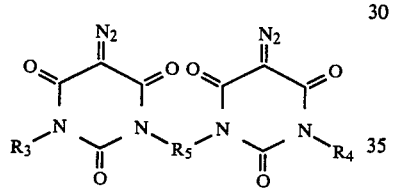

wherein $R_1$ and $R_2$ are substituents selected from the group consisting of $C_3$ to $C_{12}$ alkyl, cyclohexyl, benzyl and $C_2$ to $C_6$ aralyl groups, $R_3$ and $R_4$ are substituents selected from the group consisting of $C_1$ to $C_{12}$ alkyl, cyclohexyl, benzyl and $C_2$ to $C_6$ aralkyl groups and $R_5$ is selected from the group consisting of $\alpha,\omega$-disubstituted $C_2$ to $C_{12}$ alkyl, methylene dichyclohexyl or $C_1$ to $C_6$ dialkylphenylene;

(b) admixed with (a) from about 65 percent to about 98 dry weight percent of an aqueous alkaline soluble resin; and (c) a solvent in an amount capable of dissolving (a) and (b).

2. The composition of claim 1 wherein the resin (b) is 4-tert-butylstyrene/maleimide copolymer.

3. The composition of claim 1 wherein the solvent (c) is diglyme.

4. The method of claim 1 wherein the photosensitive barbituric acid compound is 1,3-dicyclohexyl-5-diazobarbituric acid.

5. The composition of claim 1 wherein the photosensitive barbituric acid compound is 1,12-bis(3-[1-cyclohexyl-5-diazo-2,4,6(1H,3H,5H)-pyrimidinetrionyl]) dodecane.

6. The method of claim 1 wherein the photosensitive barbituric acid compound is 1,12-bis(3-[1-n-butyl5-diazo-2,4,6(1H,3H,5H)-pyrimidinetrionyl])dodecane.

7. The method of claim 1 wherein the photosensitive barbituric acid is 1-(1-butyl)-3-cyclohexyl-5-diazobarbituric acid.

8. The method of claim 1 wherein the photosensitive barbituric acid is the bichromophoric compound of the general formula II where $R_3$ and $R_4$ are cyclohexyl and $R_5$ is methylene dicyclohexyl.

9. An intermediate element for a photosensitive device comprising a substrate containing thereon a layer of a phtoresist composition of:

(a) from about 2 to about 35 dry weight percent of a substituted derivative of 5-diazobarbituric acid selected from those exhibiting only DUV absorption and having the structural formulas:

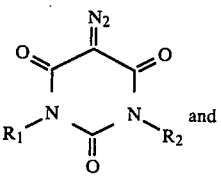

and

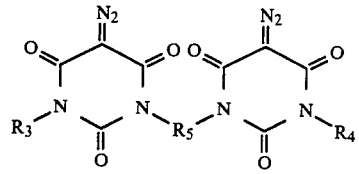

wherein $R_1$ and $R_2$ are substituents selected from the group consisting of $C_3$ to $C_{12}$ alkyl, cyclohexyl, benzyl and $C_2$ to $C_6$ aralyl groups, $R_3$ and $R_4$ are substituents selected from the group consisting of $C_1$ to $C_{12}$ alkyl, cyclohexyl, benzyl and $C_2$ to $C_6$ aralkyl groups and $R_5$ is selected from the groups consisting of $\alpha,\omega$-disubstituted $C_2$ to $C_{12}$ alkyl, methylene dicyclohexyl or $C_1$ to $C_6$ dialkyl phenylene;

(b) admixed with (a) from about 65 percent to about 98 dry weight percent of an aqueous alkali soluble resin.

10. The element of claim 9 wherein the substituted derivative of the diazobarbituric acid is 1,3-dicyclohexyl-5-diazobarbituric acid.

11. The element of claim 9 wherein the substituted derivative of the diazobarbituric acid is 1,12-bis(3-[1-cyclohexyl-5-diazo-2,4,6(1H,3H,5H)-pyrimidinetrionyl])dodecane.

12. The element of claim 9 wherein the substituted derivative of the diazobarbituric acid is 1,12-bis(3-[1-n-butyl-5-diazo-2,4,6(1H,3H,5H)-pyrimidinetrionyl])dodecane.

13. The element of claim 9 wherein the photosensitive barbituric acid is 1-(1-butyl)-3-cyclohexyl-5-diazobarbituric acid.

14. The element of claim 9 wherein the photosensitive barbituric acid is the bichromophoric compound of the general formula II where $R_3$ and $R_4$ are cyclohexyl and $R_5$ is methylene dicyclohexyl.

* * * * *